United States Patent [19]

Grover

[11] Patent Number: 5,643,921

[45] Date of Patent: Jul. 1, 1997

[54] CARDIOPULMONARY BYPASS AND ORGAN TRANSPLANT USING A POTASSIUM CHANNEL ACTIVATOR

[75] Inventor: Gary J. Grover, Stockton, N.J.

[73] Assignee: E.R. Squibb & Sons, Inc., Princeton, N.J.

[21] Appl. No.: 589,224

[22] Filed: Sep. 26, 1990

[51] Int. Cl.⁶ .......... A61K 31/44; A61K 31/35; A61K 31/495; A61K 31/535

[52] U.S. Cl. .......... 514/302; 514/456; 514/255; 514/392; 514/235.5; 514/337; 540/484

[58] Field of Search .......... 514/302, 456, 514/255, 392, 235.5, 337; 540/484

[56] References Cited

U.S. PATENT DOCUMENTS

| | | | |
|---|---|---|---|
| 4,975,444 | 12/1990 | Danilewicz et al. | 514/314 |
| 5,011,837 | 4/1991 | Atwal | 514/227.8 |
| 5,032,591 | 7/1991 | Evans et al. | 514/254 |
| 5,061,813 | 10/1991 | Atwal et al. | 549/399 |
| 5,140,031 | 8/1992 | Atwal et al. | 514/320 |

FOREIGN PATENT DOCUMENTS

| | | |
|---|---|---|
| 0351767 | 1/1990 | European Pat. Off. . |
| 354553 | 2/1990 | European Pat. Off. . |
| 401010 | 2/1990 | European Pat. Off. . |

OTHER PUBLICATIONS

F. Gharagozloo et al., *J. of Thoracic and Cardiovascular Surgery*, vol. 77, No. 4, Apr. 1979, pp. 602–607.

F. Gharagozloo et al., *Cardiac Transplantation*, vol. 76, (supp V), Nov. 1987, pp. V–65 to V–70.

H. Kohno et al., *J. Thorac. Cardiovasc. Surg.*, vol. 93, No. 1, Jan. 1987, pp. 86–94.

GA: vol. 105 (1986): 91027(8) Sakamoto.

*Primary Examiner*—Theodore J. Criares
*Attorney, Agent, or Firm*—Theodore R. Furman, Jr.; Ellen K. Park

[57] ABSTRACT

In accordance with the present invention novel methods for cardiopulmonary bypass and organ transplant, each employing a potassium channel activator, are disclosed. The use of a potassium channel activator has been found to reduce the damage or ischemia induced by the bypass and transplant procedures.

12 Claims, No Drawings

CARDIOPULMONARY BYPASS AND ORGAN TRANSPLANT USING A POTASSIUM CHANNEL ACTIVATOR

BACKGROUND OF THE INVENTION

Cardiopulmonary bypass and heart transplant are two important surgical procedures used by cardiac surgeons. While they both are designed to improve cardiac functional status, the techniques could be greatly improved. In both cases, the procedures require that the hearts be removed from the normal circulation of the body and thus by definition, some degree of damage may be observed. In bypass and transplant, cardioplegic solution, rather than blood, are employed to perfuse the coronary arteries. Accordingly, the conditions and attendant risks/damage resulting from these procedures may differ from coronary stenosis induced damage. To reduce the degree of surgical damage, the hearts are perfused in a retrograde fashion with a cardioplegic solution designed to reduce energy needs of the tissue by arresting the hearts, making them hypothermic (reduce energy demands) and also supplying them with essential substrates. While such solutions are helpful, further improvements in the ability of these hearts to compensate for the surgical damage would be useful. Cardiopulmonary bypass involves aortic cross-clamping and retrograde infusion of cardioplegic solution while heart transplant involves removal of the heart from a donor and the heart is stored in cardioplegic solution or is retrogradely perfused using a Langendorff type system until transplant can be affected.

It has long been known that potassium leaks out of myocardial cells during ischemia and the amount of potassium which leaks out seems to be correlated with the degree of ischemic damage. Indeed, potassium leaks out of hearts subjected to the type of global ischemia which would be seen during cardiopulmonary bypass and heart transplant. Current thinking indicates that compounds which could block the outward flux of potassium, i.e., potassium channel blockers, could protect the ischemic tissue.

SUMMARY OF THE INVENTION

In accordance with the present invention novel methods for organ surgery such as cardiopulmonary bypass and organ transplant, each employing a potassium channel activator, are disclosed. The use of a potassium channel activator has been found to reduce the damage or ischemia induced by the bypass and transplant procedures.

DETAILED DESCRIPTION OF THE INVENTION

In carrying out cardiopulmonary bypass and heart transplant according to the present invention, a potassium channel activator is added to any solution used to perfuse the coronary arteries or used in conection with bypass and transplant procedures. These solutions may be selected from any of the various cardioplegic solutions, intracellular solutions, etc., which are used to perfuse the arteries, to store the organ, to arrest the heart for transplant, etc. Additionally, the present invention encompasses administration of a potassium channel activator to a mammalian specie, i.e., monkey, dog, cat, rat, human, etc., which is involved in the bypass or transplant procedure. For example, a potassium channel activator can be administered to a bypass patient, organ donor and/or organ recipient before, during and/or after the bypass or transplant procedure.

In a preferred embodiment the present methods involve the use of a potassium channel activator which has little or no vasodilating effect on normal tissue. Such selective compounds have been found to open only the potassium channels in ischemic tissue and therefore such compounds offer protection of the organ for bypass- or transplant-induced ischemic damage, but have little or no blood pressure lowering activity on the patient.

While the present invention relating to transplant procedures is most frequently described in terms of heart transplant, the methods of this invention are meant to include other types of organ transplant as well. Organ transplant procedures which would also benefit from use of a potassium channel activator, especially the ischemia selective activators, include liver and kidney transplants.

Any potassium channel activator may be used in accordance with the present invention. Suitable potassium channel activators include those disclosed in U.S. Pat. No. 4,057,636, especially the compound

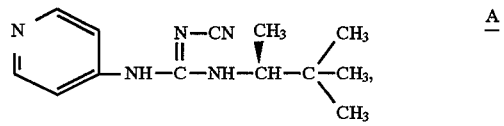

known as pinacidil; those disclosed in European Patent Application 0 274 821, especially the compound

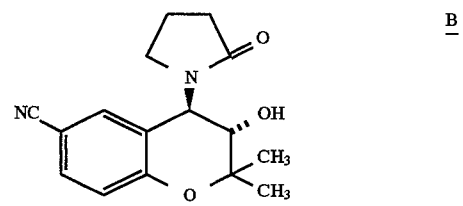

known as cromakalim; nicorandil; minoxidil; compounds in copending U.S. patent application Ser. No. 506,632 filed Apr. 9, 1990 having the formula

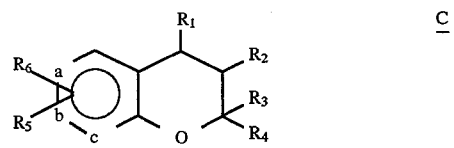

wherein a, b, and c are all carbons or one of a, b and c can be nitrogen or —NO— and the others are carbons;

$R_1$ is

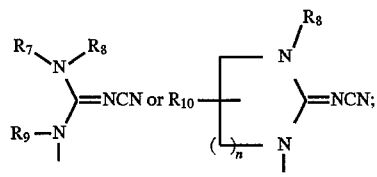

$R_2$ is hydrogen, hydroxy,

$R_3$ and $R_4$ are each independently hydrogen, alkyl, or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —$NO_2$, —COR, —COOR, —CONHR, —$CONR_2$, —$CF_3$, S-alkyl, —SOalkyl, —$SO_2$alkyl,

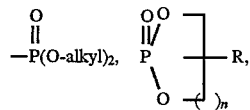

halogen, amino, substituted amino, O-alkyl, $OCF_3$, $OCH_2CF_3$, —OCOalkyl, —OCONRalkyl, —NRCOalkyl and NRCOOalkyl, $NRCONR_2$ wherein R in each of the above groups can be hydrogen, alkyl, aryl, arylalkyl, cycloalkyl, or (cycloalkyl)alkyl;

$R_6$ is selected from H, alkyl, OH, O-alkyl, amino, substituted amino, CN, and $NO_2$;

$R_7$ and $R_8$ are each independently selected from hydrogen, alkyl, alkenyl, aryl, (heterocyclo)alkyl, heterocyclo, arylalkyl, cycloalkyl and (cycloalkyl)alkyl, substituted alkyl wherein the substituents include alkoxy, alkylthio and substituted amino, or $R_7$ and $R_8$ taken together with the nitrogen atom to which they are attached form 1-pyrrolidinyl, 1-piperidinyl, 1-azepinyl, 4-morpholinyl, 4-thiamorphilinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl;

$R_9$ and $R_{10}$ are selected from hydrogen, alkyl, alkenyl, aryl, arylalkyl, cycloalkyl or cycloalkylalkyl; and n is 1, 2 or 3;

with the compound

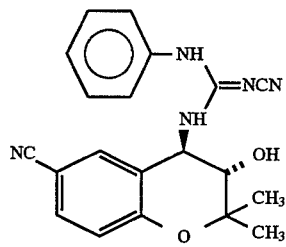

being preferred; compounds in copending application U.S. Ser. No. 349,021 filed May 8, 1989 having the formula

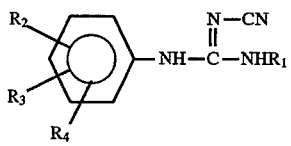

and its possible tautomers

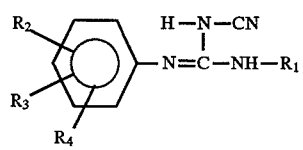

and

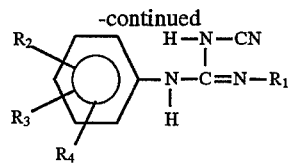

including pharmaceutically acceptable salts;

wherein $R_1$ is alkyl, alkenyl, alkynyl, haloalkyl, cycloalkyl, aryl, arylalkyl or cycloalkylalkyl;

$R_2$ is —C≡N, —$NO_2$,

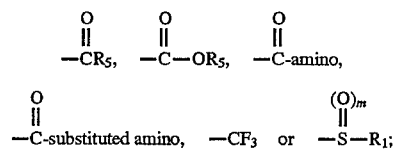

$R_3$ and $R_4$ are each independently selected from —$R_2$, hydrogen, alkyl, alkenyl, alkynyl, haloalkyl, halo, alkoxy, —NHalkyl, —N—(alkyl)$_2$, —S—alkyl, —O—arylalkyl, —S—arylalkyl or —S—aryl, —O—aryl, —NHarylalkyl, or $R_2$ and $R_3$ taken together are a group which forms a ring with the two carbon atoms to which they are attached, which group is selected from

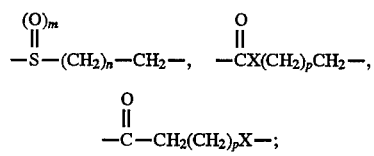

wherein m=1 or 2, n=3–5, p=2–4,

X is O, $NR_5$, $CH_2$; and $R_5$ is hydrogen or $R_1$;

compounds in copending U.S. patent application Ser. No. 540,423 filed Jun. 18, 1990 having the general formula

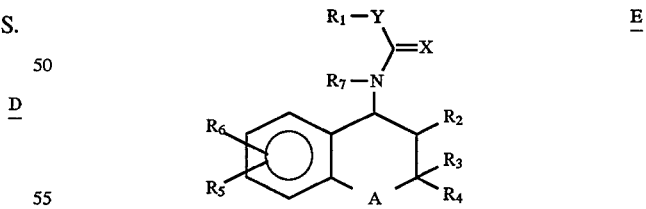

wherein A can be —$CH_2$—, —O—, —$NR_9$—, —S—, —SO— or —$SO_2$—, where $R_9$ is hydrogen or lower alkyl of 1 to 4 carbons;

wherein X is oxygen or sulfur;

Y is —$NR_8$, —O—, —S— or

$R_1$ is aryl, arylalkyl, heterocyclo or (heterocyclo)alkyl;

$R_2$ is hydrogen, hydroxy, $$-\underset{\underset{O}{\|}}{O}CCH_3;$$

$R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl, $$-\overset{O}{\underset{\|}{P}}(O\text{-alkyl})_2, \quad -\overset{O}{\underset{\underset{O-(CH_2)_n}{\diagdown}}{\overset{\|}{\underset{\diagup}{P}}}}\!\!-\!\!R,$$

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;

$R_6$ is selected from H, alkyl, halo, OH, O-alkyl, amino and substituted amino;

$R_7$ and $R_8$ are each independently selected from hydrogen, alkyl, arylalkyl;

n is 1, 2 or 3; and, $R_{10}$ is hydrogen, hydroxy, alkyl or O-alkyl; and compounds in copending U.S. patent application Ser. No. 502,967 filed Apr. 2, 1990 having the general formula $$\begin{array}{c} R_1-X \\ \diagup \\ R_7-N \end{array}\!\!=\!\!NCN \quad\quad \underline{F}$$

[structure with R$_6$, R$_5$, a, b, c ring, R$_2$, R$_3$, O, R$_4$]

wherein a, b, and c are all carbons or one of a, b and c can be nitrogen or —NO— and the others are carbons;

where X is oxygen or sulfur;

$R_1$ is selected from aryl, arylalkyl, (heterocyclo)alkyl, heterocyclo, cycloalkyl and (cycloalkyl)alkyl.

$R_2$ is hydrogen, hydroxy, $$-\underset{\underset{O}{\|}}{O}CCH_3;$$

$R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl, $$-\overset{O}{\underset{\|}{P}}(O\text{-alkyl})_2, \quad -\overset{O}{\underset{\underset{O-(CH_2)_n}{\diagdown}}{\overset{\|}{\underset{\diagup}{P}}}}\!\!-\!\!R,$$

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;

$R_6$ is selected from H, alkyl, OH, O-alkyl, amino, substituted amino, CN, and NO$_2$;

$R_7$ is selected from hydrogen, alkyl, alkenyl, aryl, arylalkyl, cycloalkyl or cycloalkylalkyl; and, n is 1, 2 or 3.

As discussed above, it has been found that compounds of formula C, E and F are extremely useful and preferred in the present methods of bypass and transplant since they have been shown to reduce LDH release in globally ischemic rat hearts while little or no reduction in blood pressure would be expected in whole animals. These and other "ischemia selective" compounds are a class of compounds wherein anti-ischemic effects comparable to the potent vasodilator cromakalim are realized, but with significantly reduced vasodilatory action.

Thus, the most preferred compounds which are those having IC$_{50}$ (rat aorta) values greater than cromakalim (as shown in the examples), i.e. those having the highest degree of selectivity, are compounds of formula C wherein $R_7$ is aryl, arylalkyl, heteroaryl or heteroarylalkyl; and compounds of formula E and F where $R_1$ is aryl, arylalkyl, heteroaryl or heteroarylalkyl.

In accordance with the present methods, the potassium channel activator is added to the cardioplegic solution utilized to perfuse the coronary arteries during bypass, and is added to the cardioplegic solutions for arresting and storage of the heart or other organ for transplant. The present methods additionally include the administration of a potassium channel activator to the bypass patient before and/or during and/or after surgery or administration to recipients and donors before and/or after transplant.

When administered to the mammalian organ donor or recipient or bypass patient, the dosage of potassium-channel activator should be in the range of 1–50 mg/kg. Administration to donor/recipient can be by any techniques known in the medical arts, e.g., orally, parenterally, intranasally, transdermally and the like, using known pharmaceutically acceptable formulations and delivery systems. This can be accomplished by compounding about 10 to 500 milligrams of a potassium channel activator into a pharmaceutically acceptable carrier by known techinques.

The potassium-channel activator can be present in the cardioplegic solutions in concentrations from about 3 μM to 60 μM and preferably is present in an amount ranging from 7 μM to 30 μM.

Grover et al., "Dissociation of Cardiodepression from Cardioprotection with Calcium Antagonists: Diltiazem Protects Ischemic Rat Myocardium with a Lower Functional Cost as Compared with Verapamil and Nifedipine", *Journal of Cardiovascular Pharmacology*; pages 331–340, Vol. 14, No. 2 (1989), describe a model for testing globally ischemic, isolated rat hearts. This model is expected to be a reliable indicator of protection since the laboratory-induced isolation and ischemic event including perfusion with a cardioplegic solution, reasonably duplicates the environment and conditions for the heart during bypass and transplant. Grover et al. express the efficacy of protective agents as the amount of lactate dehydrogenase (LDH) release and post-ischemic cardiac function. Lactate dehydrogenase is an enzyme released in the heart during an ischemic event and is an index of cardiac cell necrosis. In the Grover et al. model, this is measured during reperfusion and an agent which provides for lower release levels of LDH is considered to offer greater cardioprotection since lower LDH indicates a smaller infarct size. Cardiac function is determined using the double product (DP) of heart rate times the left ventricular developed pressure (LVDP) divided by 1,000.

The lower the value for DP before the ischemic isolation of the heart for a given agent, the more cardiodepressant it is considered to be and the higher the value of DP is during reperfusion, the more cardioprotective the agent is.

The following Example examines cromakalim, a potassium channel activator having vasodilator/blood pressure lowering activity, and compounds from formula C, E and E, which have little or no vasodilating activity in normal tissue.

Compounds Tested in Example

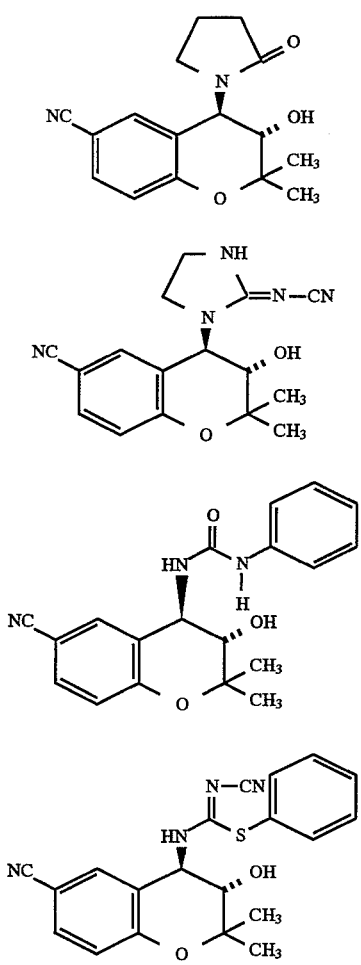

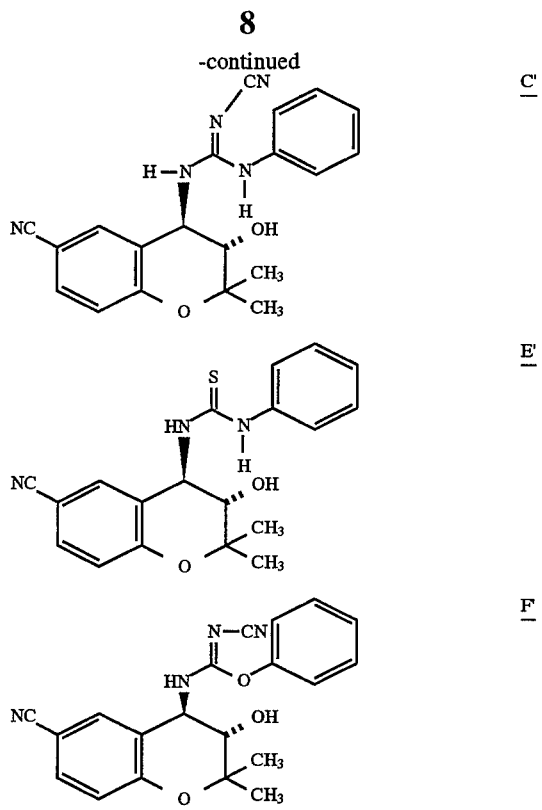

EXAMPLE

Preparation of the Isolated Perfused Hearts

Male Sprague-Dawley rats (450–550 g) were used in all experiments. The rats were anesthetized using 30 mg/kg sodium pentobarbital (i.p.). They were intubated and then treated with i.v. heparin (1000 U/kg). While being mechanically ventilated, their hearts were perfused in situ via retrograde cannulation of the aorta. The hearts were then excised and quickly moved to a Langendorff apparatus where they were perfused with Krebs-Henseleit bicarbonate buffer (112 mM $NaCl_2$, 25 mM $NaHCO_3$, 5 mM KCl, 1.2 mM $MgSO_4$, 1 mM $KH_2PO_4$, 1.25 mM $CaCl_2$, 11.5 mM dextrose, and 2 mM pyruvate bubbled with 95% $O_2$–5% $CO_2$) at a constant pressure (75 mm Hg). A water filled latex balloon attached to a metal cannula was then inserted into the left ventricle and connected to a Statham pressure transducer for measurement of left ventricular pressure. The hearts were allowed to equilibrate for 15 minutes at which time end diastolic pressure (EDP) was adjusted to 5 mm Hg and this was maintained for 5 minutes. Pre-ischemia or pre-drug function, heart rate and coronary flow (extracorporeal electromagnetic flow probe, Carolina Medical Electronics, King, N.C.) were then measured. Cardiac function was determined using the double product of heart rate (HR) X left ventricular developed pressure (LVDP) divided by 1000. Cardiac temperature was maintained throughout the experiment by submerging the hearts in 37° C. buffer which was allowed to accumulate in a stoppered, heated chamber.

Experimental Protocol

Once the baseline measurements were taken, the hearts were treated with 10 μM cromakalim, compounds C', C", E', E", F', F" (n=4 each) or with vehicle buffer (0.01% DMSO, n=7). All of these hearts were treated with their respective drugs or vehicle for ten minutes. At this time, post-drug cardiac function and flow were measured and then the hearts were made globally ischemic by shutting off the buffer perfusion. The ischemia was maintained for 25 minutes, the hearts were then reperfused with nondrug treated buffer. Reperfusion was maintained for a total of 30 minutes and at this time reperfusion function and flow were again determined. The results are summarized in the TABLE below.

Also included in the TABLE are the $IC_{50}(m)$ values for rat aorta. The $IC_{50}$ (rat aorta) value is the concentration of the particular compound which inhibits agonist-induced constriction in rat aorta by 50 percent. Thus, the lower values indicate greater vasodilation and it should be noted that these values are for normal, i.e., non-ischemic, tissue. It can be seen that cromakalim with an $IC_{50}$ of $5.7 \times 10^{-8}$ m is a relatively potent vasodilator in non-ischemic tissue. The ischemia selective compounds, however, are comparable in the anti-ischemic effects (LDH) but have only a fraction of the vasodilator action in non-ischemic tissue.

TABLE

Protective Effect of Potassium Channel Activators
Ischemic Isolated Rat Heart

| Compound | Pre-ischemic Event (Post Drug) | | | | Reperfusion (Post-Ischemic Event) | | | | | $IC_{50}$ (m) |
|---|---|---|---|---|---|---|---|---|---|---|
| | HR | LVDP | DP | FLOW | HR | LVDP | DP | FLOW | LDH | Rat Aorta |
| Vehicle | 245 | 144 | 35.5 | 15.5 | 186 | 28 | 5.6 | 14.7 | 21.94 | — |
| Cromakalim | 250 | 131 | 33.0 | 23.9 | 234 | 87 | 20.5 | 13.9 | 8.89 | $5.7 \times 10^{-8}$ |
| C' (33,812) | 244 | 134 | 32.7 | 15.2 | 244 | 74 | 18.2 | 13.2 | 10.41 | $1.37 \times 10^{-6}$ |
| C" (34,061) | 250 | 121 | 29.8 | 20.4 | 240 | 62 | 14.8 | 10.1 | 9.88 | $4.47 \times 10^{-7}$ |
| E' (34,629) | 236 | 141 | 32.75 | 15.3 | 229 | 55 | 14.83 | 13.4 | 13.46 | $1.71 \times 10^{-6}$ |
| E" (34,628) | 234 | 128 | 30.06 | 24.8 | 230 | 81 | 18.52 | 17.51 | 8.77 | $8.05 \times 10^{-7}$ |
| F' (34,268) | 238 | 128 | 30.5 | 16.0 | 212 | 28 | 6.2 | 10.4 | 21.7 | $>1 \times 10^{-4}$ |
| F" (34,696) | 239 | 159 | 38.02 | 28.3 | 247 | 59 | 14.72 | 13.92 | 10.65 | $4.9 \times 10^{-6}$ |

Concentration: 10 μM
Occlusion: 25 minutes
Reperfusion: 30 minutes
HR = Heart Rate
LVDP = Left Ventricular Developed Pressure (mmHg)
DP = Double Product
LDH = Lactate Dehydrogenase Release

What is claimed is:

1. A method for protecting an organ and surrounding cells from ischemic damage in a mammalian species subject to organ surgery which method comprises employing an organ-protecting amount of an ischemia selective potassium channel activator.

2. The method of claim 1 wherein said potassium channel activator is added to a solution used in said surgery in order to preserve, protect or maintain organ function.

3. The method of claim 1 wherein said ischemia selective potassium channel activator is selected from

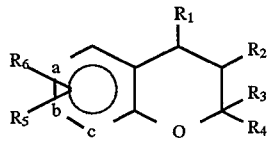

wherein a, b, and c are all carbons or one of a, b and c can be nitrogen or —NO— and the others are carbons;

$R_1$ is

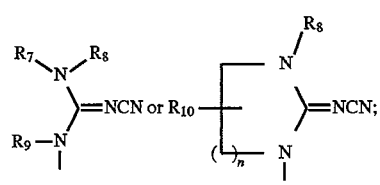

$R_2$ is hydrogen, hydroxy,

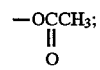

$R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —NO₂, —COR, —COOR, —CONHR, —CONR₂, —CF₃, S-alkyl, —SOalkyl, —SO₂alkyl,

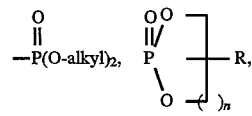

halogen, amino, substituted amino, O-alkyl, OCF₃, OCH₂CF₃, —OCOalkyl, —OCONRalkyl, —NRCOalkyl and NRCOOalkyl, NRCONR₂ wherein R in each of the above groups can be hydrogen, alkyl, aryl, arylalkyl, cycloalkyl, or (cycloalkyl)alkyl;

$R_6$ is selected from H, alkyl, OR, O-alkyl, amino, substituted amino, CN, and NO₂;

$R_7$ and $R_8$ are each independently selected from aryl, (heterocyclo) alkyl, heterocyclo, arylalkyl, wherein the term "aryl" refers to phenyl, 1-naphthyl, 2-naphthyl or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, CF$_3$, —OCHF$_2$,

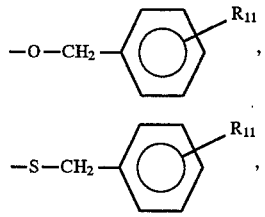

(wherein R$_{11}$ is hydrogen, alkyl of 1 to 4 carbons, alkoxy of 1 to 4 carbons, alkylthio of 1 to 4 carbons, halo, hydroxy of CF$_3$), —O—CH$_2$-cycloalkyl, or —S—CH$_2$-cycloalkyl, and di-substituted phenyl, 1-naphthyl, 2-naphthyl wherein said substituents are selected from methyl, methoxy, methylthio, halo, CF$_3$, nitro, amino and OCHF$_2$;

R$_9$ and R$_{10}$ are selected from hydrogen, alkyl, alkenyl, aryl, arylalkyl, cycloalkyl or cycloalkylalkyl; and n is 1, 2 or 3;

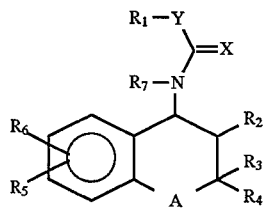

wherein A can be —CH$_2$—, —O—, —NR$_9$—, —S—, —SO— or —SO$_2$—, where R$_9$ is hydrogen or lower alkyl of 1 to 4 carbons;

wherein X is oxygen or sulfur;

Y is —NR$_8$, —O—, —S— or

R$_1$ is aryl, arylalkyl, heterocyclo or (heterocyclo)alkyl;

R$_2$ is hydrogen, hydroxy,

R$_3$ and R$_4$ are each independently hydrogen, alkyl or arylalkyl, or, R$_3$ and R$_4$ taken together with the carbon atom to which they are attached form a 5- to 7-membered carbocyclic ring;

R$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

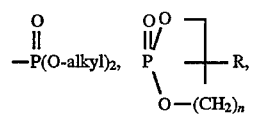

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;

R$_6$ is selected from H, alkyl, halo, OH, O-alkyl, amino and substituted amino;

R$_7$ and R$_8$ are each independently selected from hydrogen, alkyl, arylalkyl;

n is 1, 2 or 3; and,

R$_{10}$ is hydrogen, hydroxy, alkyl or O-alkyl; and compounds in copending U.S. patent application Ser. No. 502,967 filed Apr. 2, 1990 having the general formula

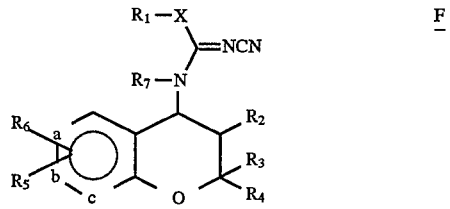

wherein a, b, and c are all carbons or one of a, b and c can be nitrogen or —NO— and the others are carbons;

where X is oxygen or sulfur;

R$_1$ is selected from aryl, arylalkyl, (heterocyclo)alkyl, heterocyclo;

R$_2$ is hydrogen, hydroxy,

R$_3$ and R$_4$ are each independently hydrogen, alkyl or arylalkyl, or, R$_3$ and R$_4$ taken together with the carbon atom to which they are attached form a 5- to 7-membered carbocyclic ring;

R$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

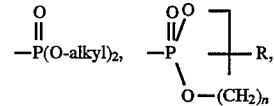

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl, aryl, arylalkyl, cycloalkyl, or (cycloalkyl)alkyl;

R$_6$ is selected from H, alkyl, OH, O-alkyl, amino, substituted amino, CN, and NO$_2$;

R$_7$ is selected from hydrogen, alkyl, alkenyl, aryl, arylalkyl, cycloalkyl or cycloalkylalkyl; and, n is 1, 2 or 3.

4. The method of claim 3 wherein said ischemia selective potassium channel activator has the formula

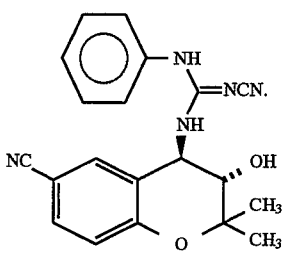

5. The method of claim 3 wherein said ischemia selective potassium channel activator is selected from

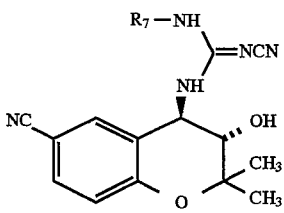

wherein $R_7$ is phenyl, mono-substituted phenyl or disubstituted phenyl.

6. The method of claim 1 wherein said surgery is cardiopulmonary bypass surgery.

7. The method of claim 1 wherein said surgery is organ transplant surgery.

8. The method of claim 7 wherein said surgery is heart transplant surgery.

9. The method of claim 1 wherein said ischemia selective potassium channel activator is administered to said mammalian species before and/or during and/or after said organ surgery.

10. The method of claim 2 wherein said organ-protecting amount of said potassium channel activator is added to a cardioplegic solution used in arrest, perfuse, store and/or protect a heart involved in a cardiopulmonary bypass or heart surgery.

11. The method of claim 1 wherein said ischemia selective potassium channel activator is administered to said mammalian species before and/or during and/or after said organ surgery.

12. The method of claim 1 wherein said ischemia selective potassium channel activator is administered to said mammalian specie before, during or after said organ surgery.

* * * * *